United States Patent [19]

Burstein et al.

[11] 4,064,567

[45] Dec. 27, 1977

[54] PROSTHESIS-TO-BONE INTERFACE SYSTEM

[75] Inventors: Albert H. Burstein, Greenwich, Conn.; Bertram L. Koslin, Yorktown Heights, N.Y.

[73] Assignee: The Sampson Corporation, Pittsburgh, Pa.

[21] Appl. No.: 723,615

[22] Filed: Sept. 15, 1976

[51] Int. Cl.$^2$ ............................................. A61F 1/24
[52] U.S. Cl. ..................................... 3/1.91; 3/1.911; 3/1.913; 128/92 C; 128/92 CA
[58] Field of Search ................................. 3/1.9–1.913, 3/1; 128/92 C, 92 CA, 92 R, 92 B, 92 G

[56] References Cited

U.S. PATENT DOCUMENTS

| 3,793,650 | 2/1974 | Ling et al. | 3/1.91 |
| 3,820,167 | 6/1974 | Sivash | 3/1.912 |
| 3,848,273 | 11/1974 | Frey | 128/92 CA |

FOREIGN PATENT DOCUMENTS

| 2,404,214 | 8/1974 | Germany | 3/1.9 |

OTHER PUBLICATIONS

Vitallium Surgical Appliances, (Catalog) by Austenal Co., New York, N.Y., 1964, p. 65, Vitallium Wire Mesh No. 6510 relied upon.

*Primary Examiner*—Ronald L. Frinks
*Attorney, Agent, or Firm*—Dennison, Dennison, Meserole & Pollack

[57] ABSTRACT

A woven basket is placed over the stem of a prosthesis and receives bone cement therewithin and through its intersticies. The resulting prosthesis-to-bone interface greatly improves the distribution of forces transferred to the bone.

13 Claims, 11 Drawing Figures

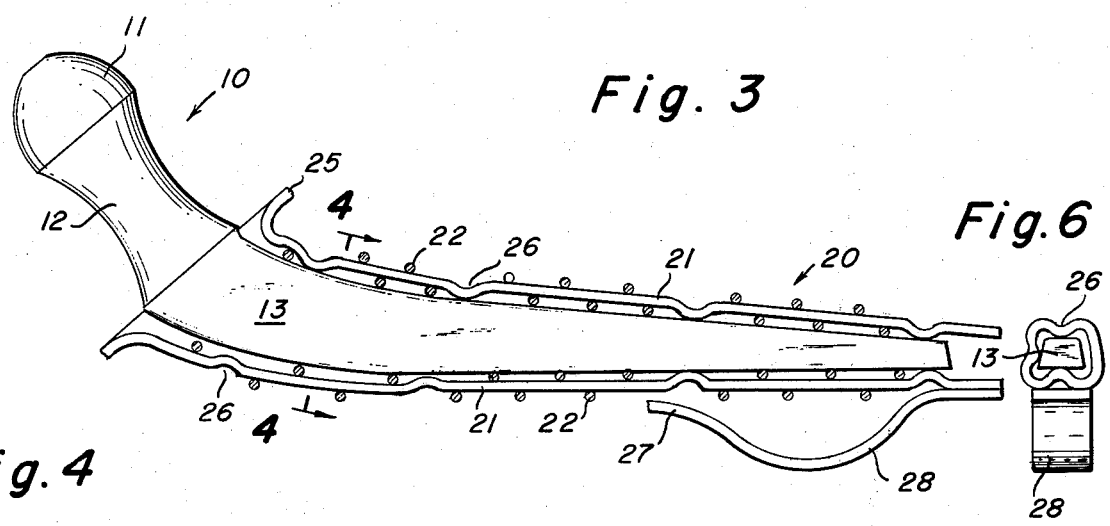
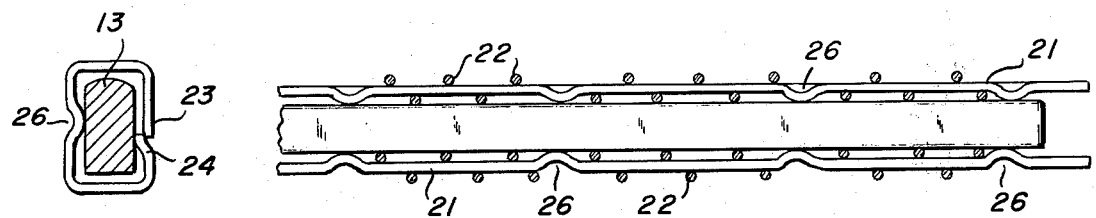
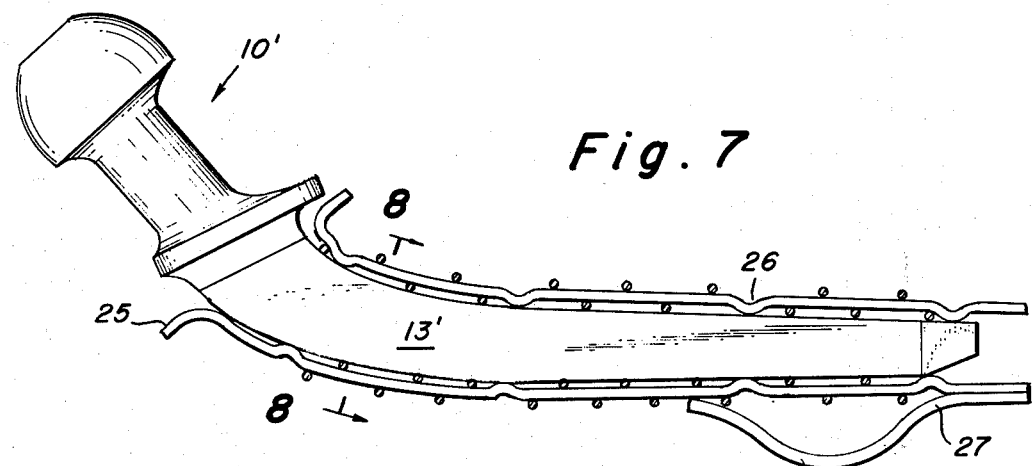
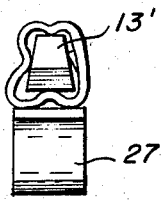
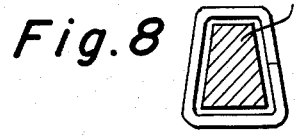

PROSTHESIS-TO-BONE INTERFACE SYSTEM

BACKGROUND OF THE INVENTION

This invention relates broadly to means for transferring forces imposed on load bearing portions of artificial joints to bone in humans and animals. While the present invention is applicable for use with implants of various types and in numerous applications in human and animal joints, it will be described herein for purposes of example only specifically as adapted for use in transferring the load on the femoral head replacement of a total hip joint prosthesis such as the Charnley type, to the femur. Although hip prostheses will be used for illustrative purposes only, features of the invention will be stated in a generic form so that they are applicable to all joint prostheses and to the geometric and biomedical properties of all animal and human joints.

One of the fundamental problems that has been encountered in the development of prosthetic replacements for the major joints of the body is the means utilized for attaching the implant to bone. Various forms of joint prostheses currently used are held in place in the body commonly by one of three methods: (1) a stem which is impacted into the medullary canal of the bone; (2) a stem which is fixed mechanically by internal fixation as provided by bone screws, pins, or the like; and (3) a stem which is fixed by bone cements, grouts or adhesives such as polymethylmethacrylate which is polymerized in situ and serves as a cement or filler between the stem of the prosthesis and the bone.

Each of these methods currently in use has presented problems that can lead to failure of the arthroplasty. The problems are as follows:

Devices that are impacted into the medullary cavity of the bone are held in place by the surrounding bone. The actual surface of contact between the prosthesis and the bone may be very small and areas of stress concentration will frequently occur. Clinical observations have been reported associating loosening of the implant (due principally to bone resorption) and joint pain.

Historically, when mechanical internal fixation has been used, clinicians take exception to the difficulties of inserting the implant and to the long term inadequacy of the fixation of the implant to bone which results in patient discomfort.

Polymethylmethacrylate, when polymerized in situ, will initially secure stems of total joint prostheses firmly in place allowing the patient to use the joint without pain. However, there is growing clinical evidence concerning the long term efficacy of this form of fixation. Three kinds of the most frequent failure modes of polymethylmethacrylate fixation which are associated with prosthesis stem failure are: (1) improper (varus) placement of the stem at the time of surgery; (2) breakdown, cracking and dislocation of the cement; and (3) resorption of bone tissue with the associated loosening of the cement-bone fixation.

In each instance, a prosthesis stem fails because of the excessive loads on the stem due to the change in the support and transfer mechanism between stem, cement and bone. Tensile stressses in the stem, e.g., the lateral surface of a hip prosthesis stem, due to the bending moment imposed by a patient's weight or muscle contractions, will lead to fatigue failure under repetitive cyclic loading. Typically, a fatigue crack will initiate in the region subjected to high tensile stress and will propagate through the stem cross-section by slow crack growth until the metal in the remaining cross-section is insufficient to support the loads, thereafter rapid cracking will occur through this remaining cross-section. Also, ordinary state-of-the-art difficulties in manufacture cause discontinuity in the metals such as voids, inclusions, notches and scratches, and accordingly these areas are sites for potential crack initiation.

Attempts have been made to reduce the stress level in the stems of various prostheses by design modification. For example, the neck length and neck shaft angle of the hip prostheses have been modified. A simple way to decrease the stress in stems is to increase the section modulus of the stem. Because this provides a bulky, heavy, more rigid prosthesis, problems of insertion are encountered as the section modulus is increased.

We believe that it is not ideal to have a relatively rigid stem and in fact the preferred way to transfer the load from bone to the prosthesis and then to bone is by using a stem with lower relative rigidity, directly contrary to teachings of the prior art.

The more directly load can be transferred from bone to the load bearing portion of the implant to bone, the more natural will be the bone's reaction thereto, therefore less resorption will occur, and more bone material will be retained. The lower rigidity stem(s) facilitate transfer of the load out of and then into the bone more directly, rather than carrying load down (or up) to the tip of the prosthesis before transferring it to bone. In order to utilize the presently available stems, especially those of lower relative rigidity, more effectively, there must be a change in the mechanical properties of the presently used method to interface the stems with bone. The present invention (a device) is inserted between the stem(s) and bone together with polymethylmethacryate or similar cement materials and is capable of deforming and efficiently transferring the load into the bone. The device produces a new interface system which will not break up with presently available (or less rigid) stem(s), and provides a system that has increased strength and can undergo larger deflections than is the case with the simple use of polymethylmethacryalte alone.

Until now, emphasis has been placed on providing extra strength in the stems of prostheses, usually in the form of extra thickness. The present invention overcomes the problems prevalent in the prior art, specifically in the use of polymethylmethacryalte which has a low modulus, low strength and is extremely brittle. It of course has been noted that when the polymethylmethacrylate fails, the implant often fails.

OBJECTS AND SUMMARY OF THE INVENTION

Bearing in mind the above problems inherent in the prior art, our invention has provided an improved means for transferring the forces imposed on load bearing artificial joint surfaces to bone by using a high modulus ductile material in suitable form for conforming to and covering implant stems in combination with a cement such as polymethylmethacrylate.

A further object of this invention is to provide a device which is not primarily directly load bearing but serves mainly to transfer the load between a prosthesis and bone.

A further principal object of this invention is to provide an implantable device surrounding a prosthesis stem which is compatible with body tissue.

Yet another object of this invention is to provide a prosthesis-to-bone interface system which is relatively simple in construction, mechanically safe and efficient, reliable in use, and which produces no untoward reactions with the stems of prostheses.

Other objects and advantages will become apparent from the following description of one class of forms of the invention illustrated in the accompanying drawings. For purposes of example only, we will illustrate a realization of the invention for use in conjunction with the stems of hip prostheses. Since the device covers and conforms to the shape of different stems (including the stems of hip prostheses) we will refer to its form generically as a basket.

DESCRIPTION OF THE DRAWINGS

In order that the invention may be more fully understood, a preferred embodiment for hip prostheses in accordance therewith will now be described by way of example with reference to the accompanying drawings in which:

FIG. 3 is a view similar to FIG. 1 but showing the basket in cross-section;

FIG. 4 is a cross-section taken along the line 4—4 of FIG. 3;

FIG. 5 is a fragmentary top view of FIG. 3 showing the basket in section;

FIG. 6 is an end view of FIG. 3 as seen from the right;

FIG. 7 is a view similar to FIG. 3, but showing a modified basket placed on a different type of femoral head prosthesis;

FIG. 8 is a cross-sectional taken along the line 8—8 of FIG. 7;

FIG. 9 is a fragmentary top view of FIG. 7 showing the modified basket in section;

FIG. 10 is an end view of FIG. 7 as seen from the right; and

DESCRIPTION OF THE PREFERRED EMBODIMENT

Figure 1:
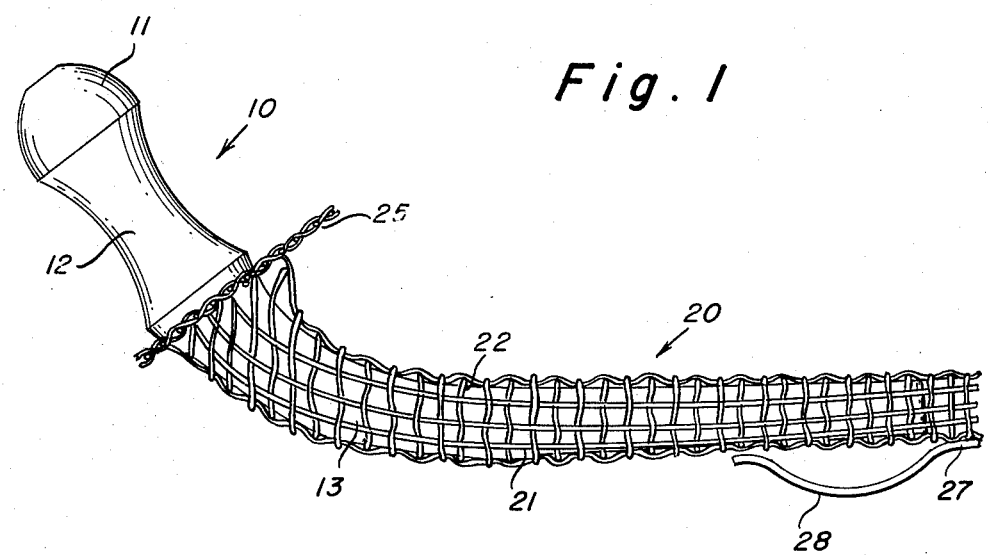
FIG. 1 is a front elevation of the basket of the present invention in place over the femoral stem of a Charnley prosthesis.
Figure 2:
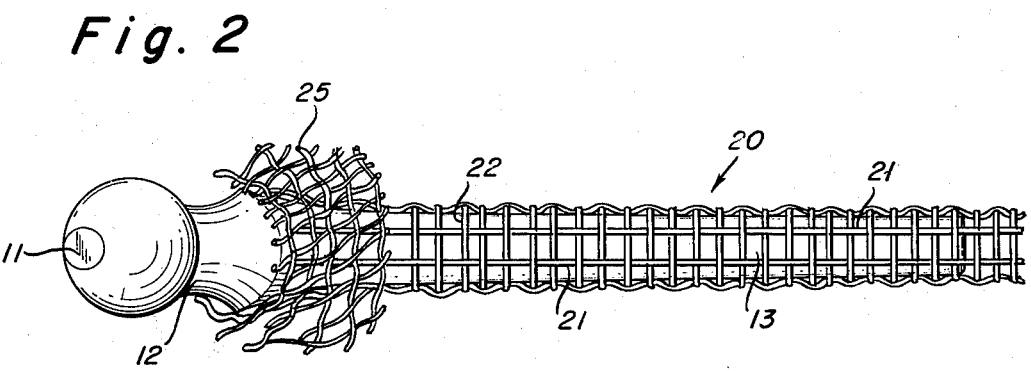
FIG 2. is a top view of the basket and stem of FIG. 1.

Referring to the drawings wherein the reference characters represent like parts, the conventional Charnley femoral head prosthesis is shown generally at 10 and includes a generally spherical head 11, a neck 12 and a tapered stem 13. The stem may take many different forms as shown for example at 13' in the modification 10' of FIGS. 7–10 which depict the well known T-28 stem. This stem is of trapezoidal cross-section throughout. The head, neck and stem are formed from metals which are compatible with the human body such as a chrome-cobalt alloy, 316 L stainless steel, titanium, or other compatible materials.

The principal element of our new invention is a mesh sheath or basket 20 which is formed of interwoven metal wire to form an open mesh screen structure. Titanium, stainless steel and chrome-cobalt open weave mesh have been found acceptable for this purpose. It is also contemplated that screens or mesh of plastics, carbon, DACRON or KELVAR could be used.

The mesh is formed around the prosthesis stem or a similar shaped mandrel to conform generally to the shape thereof although somewhat larger to accommodate stem 13. Ideally, the screen is oriented so that the wires 21 run lengthwise and parallel to the stem and cross wires 22 generally at right angles thereto. The longitudinal wires provide basic strength, serve as crack arrestors to maintain the shape and integrity of the polymethylmethacrylate cement, and maintain the apposition of cement particles if cracks do occur. The cross wires also serve as crack arrestors, maintain the shape and integrity of the polymethylmethacrylate and maintain the apposition of cement particles if cracks do occur so that the cracked cement can still be loaded and transmit compressive forces. In addition, both sets of wires reinforce the polymethylmethacrylate or similar cements, improving their mechanical properties particularly in withstanding bending moments. In order to permit insertion of the curved stem in most sizes and styles of prostheses, it is apparent that the basket itself cannot be rigid but must be somewhat flexible. In order to properly conform to stems, the basket must have some mechanical integrity to hold its shape during insertion.

The overlapped ends of the mesh 23, 24 may be trimmed down and also formed into a dimple as shown in FIG. 4 to present a neat edge free of sharp protrusions which would otherwise tend to snag during insertion into the medullary canal of the femur.

As seen in FIG. 3, the basket is preferably of a length somewhat greater than the stem, although this is not essential and the basket coult accordingly be the same size or even slightly shorter than the stem. Adjacent the wider proximal end, the mesh is flared outwardly to provide a collar 25. This collar, although it is not essential, serves to reinforce the neck portion 12 of the prosthesis and to effect more load transfer to bone to inhibit resorption.

In order to provide some spacing of the sheath from the stem, the latter may be dimpled along its length as at 26 on all four of its faces. The size of the dimpling may be such as to prevent contact of the cross wires 22 from touching the prosthesis stem 13. Thus, the number of contact points between the basket and the prosthesis stem may be controlled. In a like manner, the mesh may be dimpled outwardly (not shown) to control the spacing between the stem and the cortical bone or shell. This provides sufficient space for the reception of the bone cement.

Figure 11:
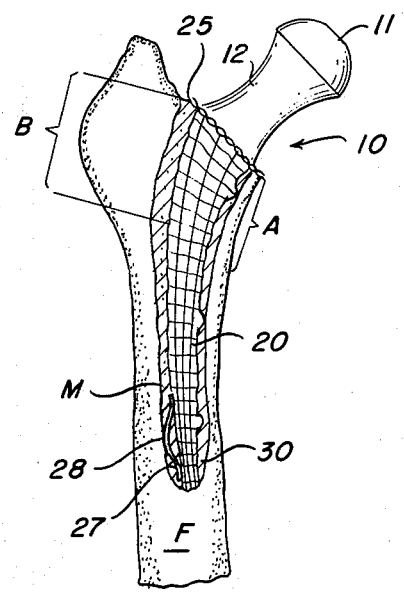
FIG. 11 is a vertical section through a human femur showing the prosthesis and interface system in place.

At the distal end of the basket, a leaf spring 27 may be secured as by welding or the like. The spring has a rather substantial bow 28. This arrangement, if used, assists in the proper and accurate installation of the prosthesis and pushes against the enlarged medullary canal of the femur F so that the implant system is offset and in contact with medial wall as shown in FIG. 11.

The insertion of the implant system (hip prostheses, basket and polymethylmethacrylate) using conventional surgical techniques, is as follows: after opening of the medullary canal of the femur by drilling and possibly shaping with a rasp, the polymethylmethacrylate M is placed in the canal 30 and an additional amount squeezed into the basket and about the collar; the stem of the prosthesis is then inserted into the basket until the neck 12 abuts the collar; the entire assembly is then inserted in the enlarged medullary canal as in FIG. 11, which has been filled with cement.

It will be apparent that the basket can be formed of different cross-sectional shapes dependent on the specific prosthesis for which it is used. FIGS. 3–6 show a basket formed to be used with a Charnley-type prosthesis. In FIGS. 7-10, a modified basket is shown on stem 13' of a T-28 prosthesis 10'.

It is apparent that the tissue compatible material out of which the basket can be fabricated can be stamped so that it has the appropriate perforations or made of any other malleable perforated sheet material. The ideal number of dimples on the basket to control both the number of contacts with the prosthesis stem as well as the number of contacts with the cortical bone is, along with the gauge of the wire mesh (or the size of the perforations), a consequence of the particular implant prosthesis.

While reference has been made to conventional hip prosthesis as has been discussed earlier, the use of the sheath or basket proposed herein will permit the use of lighter, thinner, less rigid stem prostheses than are currently being commerically produced.

The basic concepts of the invention are not to be limited to hip prostheses since the same advantage will be available when baskets of the invention are used with stems of various other prosthetic devices, such as, implanted knee joints, elbows, wrists, etc. In such instances, the basket may be fabricated in suitable geometric form (such as a cup or cylinder) to conform to the shape of the stem of a prosthesis.

We claim:

1. A prosthesis-to-bone interface comprising a sheath formed of a single thickness of a relatively rigid, malleable and intersticiated material, generally conforming in shape and adapted to receive the stem of a prosthesis therein, and means for spacing the inner wall of said sheath from said stem to define a space within which bone cement may be received.

2. An interface as defined in claim 1 and further including means for spacing the outer wall of said sheath from the cortical shell of the bone.

3. An interface as defined in claim 1 wherein said sheath is deformed inwardly at spaced points along its length forming dimples which define said means spacing the inner wall from said prosthesis stem.

4. An interface as defined in claim 2 wherein said sheath is deformed outwardly as spaced points along its length forming dimples which define said means spacing the outer wall from cortical bone.

5. An interface as defined in claim 1 and further including a widened collar at the proximal end of said sheath and formed of the same material.

6. An interface as defined in claim 1 wherein the intersticiated material is a perforated sheet formed of a metal or other high modulus ductile material compatible with the body.

7. An interface as defined in claim 1 wherein the intersticiated material is a mesh formed of a metal or other high modulus ductile wire material compatible with the body.

8. An interface as defined in claim 7 wherein said mesh wire is chrome-cobalt alloy.

9. An interface as defined in claim 7 wherein some of the mesh wires run longitudinally along the sheath axis and the remaining wires run at substantially right angles thereto.

10. An interface as defined in claim 1 and further including leaf spring means on the outer face of said sheath adjacent to the distal end thereof engageable with the medullary canal to properly space the prosthesis stem with respect thereto.

11. An interface as defined in claim 1 wherein said sheath is tubular, tapering from its proximal to its distal end.

12. An interface for strengthening the connection between a prosthetic device and human or animal bone wherein the device is adapted for insertion in a bone cavity which has been prepared to receive the same and which includes the application of a bone cement, comprising a sheath formed of a single thickness of a relatively rigid, malleable and intersticiated material, means for spacing the inner wall of said sheath from said stem to define a cement receiving space therebetween, the stem of the prosthetic device and cement substantially filling and surrounding said sheath, with cement extending through the intersticies of the sheath.

13. An interface as defined in claim 12 wherein said sheath is formed of a mesh or perforated sheet of a metal or other high modulus ductile material compatible with the body.

* * * * *